United States Patent
Mori et al.

(10) Patent No.: US 9,791,427 B2
(45) Date of Patent: Oct. 17, 2017

(54) SYSTEM AND METHOD FOR CALCULATING CONCENTRATION OF WATER TREATMENT CHEMICAL

(71) Applicant: KURITA WATER INDUSTRIES LTD., Tokyo (JP)

(72) Inventors: Shintarou Mori, Tokyo (JP); Yukimasa Shimura, Tokyo (JP)

(73) Assignee: KURITA WATER INDUSTRIE LTD., Tokyo (JP)

( * ) Notice: Subject to any disclaimer, the term of this patent is extended or adjusted under 35 U.S.C. 154(b) by 0 days.

(21) Appl. No.: 15/038,791

(22) PCT Filed: Dec. 2, 2014

(86) PCT No.: PCT/JP2014/081819
§ 371 (c)(1),
(2) Date: May 24, 2016

(87) PCT Pub. No.: WO2015/087738
PCT Pub. Date: Jun. 18, 2015

(65) Prior Publication Data
US 2017/0082591 A1     Mar. 23, 2017

(30) Foreign Application Priority Data
Dec. 10, 2013   (JP) ................................. 2013-255090

(51) Int. Cl.
*G01N 33/18*     (2006.01)
*C02F 1/00*      (2006.01)
(Continued)

(52) U.S. Cl.
CPC ............. *G01N 33/18* (2013.01); *C02F 1/008* (2013.01); *G01N 21/255* (2013.01); *G01N 21/31* (2013.01);
(Continued)

(58) Field of Classification Search
CPC ................ C02F 1/008; C02F 2103/023; C02F 2209/001; C02F 2209/006;
(Continued)

(56) References Cited

U.S. PATENT DOCUMENTS 9,134,290 B2 *   9/2015   Saini .................. G01N 33/1826

FOREIGN PATENT DOCUMENTS

JP     2000-271564 A   10/2000
JP     2003-112169 A    4/2003
(Continued)

OTHER PUBLICATIONS

Japan Patent Office, "Office Action for JP 2013-255090," Jan. 13, 2015.
(Continued)

*Primary Examiner* — Jennifer Wecker
(74) *Attorney, Agent, or Firm* — Manabu Kanesaka

(57) ABSTRACT

A system for calculating a concentration of a water treatment chemical includes a water analyzer, databases storing information regarding a chemical component of the water treatment chemical, a server sending the information stored in the database, and a communication device sending the information acquired from the server to the water analyzer. The water analyzer includes a storage unit storing a calibration curve defining the relationship between the concentration of a chemical component and absorbance, a communication unit receiving the information regarding the chemical component of the water treatment chemical, an irradiation unit irradiating water to be analyzed with light, a detection unit detecting transmitted light, and an arithmetic and control unit calculating absorbance from the result of the detection by the detection unit, acquiring a calibration curve from the storage unit, and calculating the concentration of
(Continued)

the chemical component with reference to the acquired calibration curve and the measured absorbance.

20 Claims, 3 Drawing Sheets

(51) Int. Cl.
    *G01N 21/31*     (2006.01)
    *G01N 21/25*     (2006.01)
    *G01N 21/79*     (2006.01)
    *G01N 33/44*     (2006.01)
    *G01N 21/78*     (2006.01)
    *G01N 21/75*     (2006.01)
    *C02F 103/02*     (2006.01)

(52) U.S. Cl.
    CPC .............. *G01N 21/78* (2013.01); *G01N 21/79* (2013.01); *G01N 33/442* (2013.01); *C02F 2103/023* (2013.01); *C02F 2209/001* (2013.01); *C02F 2209/006* (2013.01); *C02F 2209/008* (2013.01); *G01N 33/1826* (2013.01); *G01N 2201/12723* (2013.01)

(58) Field of Classification Search
    CPC   C02F 2209/008; G01N 21/255; G01N 21/31; G01N 21/78; G01N 21/79; G01N 2201/12723; G01N 33/18; G01N 33/442
    See application file for complete search history.

(56) References Cited

FOREIGN PATENT DOCUMENTS

| | | |
|---|---|---|
| JP | 2003-164852 A | 6/2003 |
| JP | 2003-211148 A | 8/2003 |
| JP | 2006-038462 A | 2/2006 |
| JP | 2006-308420 A | 11/2006 |
| JP | 2006308420 A * | 11/2006 |

OTHER PUBLICATIONS

PCT/ISA/210, "International Search Report for International Application No. PCT/JP2014/081819".

* cited by examiner

SYSTEM AND METHOD FOR CALCULATING CONCENTRATION OF WATER TREATMENT CHEMICAL

FIELD OF INVENTION

The present invention relates to a system and a method for calculating the concentration of a water treatment chemical charged in a water system such as a cooling water system or a boiler water system or the concentration of a chemical component of the water treatment chemical.

BACKGROUND OF INVENTION

For achieving safe and efficient operation of a plant in which water is used, it is necessary to use a water treatment chemical suitable for the plant. Accordingly, it is important to analyze and maintain the concentration of the water treatment chemical.

For example, water treatment chemicals containing an anionic polymer such as an acrylic acid polymer, an acrylic acid copolymer, a maleic acid polymer, or a maleic acid copolymer, are added to water systems such as a cooling water system and a boiler water system for the purpose of water treatment, that is, for inhibiting occurrence of scale, corrosion, contamination, and the like. Anionic polymers are high-performance scale inhibitors. For making full use of the scale-inhibiting capability of an anionic polymer, it is essential to control the concentration of the anionic polymer in the targeted water system. As a method for measuring the concentration of such an anionic polymer in water, Patent Literatures 1 and 2 describe a method in which a reagent is added to test water taken from a water system and reacted with the anionic polymer in order to make the test water cloudy, the degree of cloudiness is measured in terms of the absorbance of visible light having a wavelength of 400 to 900 nm by the test water, and the concentration of the anionic polymer is subsequently determined. The concentration of the anionic polymer is determined on the basis of the measured absorbance and a calibration curve representing the relationship between the concentration of the anionic polymer and absorbance. The calibration curve is prepared using samples of test water having known concentrations.

The measurement apparatus used in the method described in Patent Literature 1 is portable.

In general, commercially available water treatment chemicals are not composed of only water treatment chemical components, but contain, in addition to the specific water treatment chemical components (e.g., an anionic polymer), a solvent, a stabilizer, and other chemical components such as an anticorrosive and a germicide. Therefore, in the case where the content of an anionic polymer in a water treatment chemical is unknown, it is not possible to determine the concentration of the water treatment chemical in a water system even when the concentration of the anionic polymer has been determined in accordance with the method described in Patent Literatures 1 and 2.

The concentration of a water treatment chemical in a water system may be controlled in terms of the concentration of a chemical component (e.g., anionic polymer). However, there are many cases where the concentration of a water treatment chemical is directly controlled. The concentration of a water treatment chemical in a water system is determined by measuring the concentration of a chemical component in the water system and converting the concentration of the chemical component to the concentration of the water treatment chemical in the water system on the basis of the composition of the chemical. For example, data regarding the concentration of the chemical component (i.e., concentration of an anionic polymer) in the chemical are acquired from a catalog of chemicals, a product data sheet, or the like, and the concentration of the anionic polymer is converted to the concentration of the chemical on the basis of the data.

LIST OF PATENT LITERATURE

Patent Literature 1: Japanese Patent Publication 2006-38462 A

Patent Literature 2: Japanese Patent Publication 2003-164852 A

SUMMARY OF INVENTION

In the method for determining an anionic polymer described in Patent Literature 1, in the case where different types of polymers are used, the concentrations of the polymers need to be determined using different calibration curves that have been prepared using the respective polymers, because the calibration relationship between the concentration of a polymer and turbidity varies among polymers. Therefore, it is necessary to prepare the same number of sets of calibration curve data as the number of the types of polymers. It requires considerable time and effort to acquire the data.

Hitherto, as described above, the concentration of a chemical containing a polymer has been calculated by measuring the concentration of the polymer and converting the concentration of the polymer to the concentration of the chemical on the basis of the proportion of the polymer in the chemical by using a conversion table or the like. However, this method includes a complex conversion process and may increase the chance of a miscalculation.

Furthermore, when the type or proportion of a polymer contained in a chemical has changed, the calibration curve, the conversion table, and the like need to be changed accordingly. It is considerably difficult to communicate the change of the calibration curve, the conversion table, or the like to all the measurers and to change data regarding a conversion program without delay.

The present invention was made with consideration of the foregoing issues. An object of the present invention is to provide a system and a method for calculating the concentration of a water treatment chemical which enables the concentration of a water treatment chemical charged in a water system to be calculated readily.

A system for calculating a concentration of a water treatment chemical of a first invention includes a water analyzer including an absorbance measuring device for measuring absorbance of water taken from a water system containing a water treatment chemical; a database that stores information regarding a type and proportion of a chemical component of the water treatment chemical; a server that sends the information regarding the type and proportion of the chemical component of the water treatment chemical to a communication device, the information being stored in the database; and the communication device that acquires the information regarding the type and proportion of the chemical component from the server and sends the acquired information to the water analyzer. The water analyzer further includes a storage unit that stores a calibration curve defining a relationship between a concentration of a chemical component and absorbance, a communication unit that receives the information regarding the type and proportion of the chemical component of the water treatment chemical from the communication device, and an arithmetic and control unit that acquires a calibration curve from the storage unit, the calibration curve corresponding to the type of the chemical component contained in the received information, and calculates a concentration of the chemical component in the water system with reference to the acquired calibration curve and the measured absorbance or the concentration of the water treatment chemical on the basis of the concentration of the chemical component.

It is preferable in the system for calculating a concentration of a water treatment chemical that the arithmetic and control unit calculates the concentration of the water treatment chemical in the water system on the basis of the concentration of the chemical component and the proportion of the chemical component, the proportion of the chemical component being received by the communication unit.

It is preferable in the system for calculating a concentration of a water treatment chemical that the server sends data regarding a calibration curve corresponding to the chemical component of the water treatment chemical to the communication device, the communication device sends the data regarding the calibration curve to the water analyzer, the data being received from the server, and the water analyzer registers the data regarding the calibration curve in the storage unit, the data being received from the communication device via the communication unit.

A system for calculating a concentration of a water treatment chemical of a second invention includes a water analyzer including an absorbance measuring device for measuring absorbance by water taken from a water system containing a water treatment chemical, and a sending unit that sends the measured absorbance to a communication device; a database that stores information regarding a type and proportion of a chemical component of the water treatment chemical and a calibration curve defining a relationship between a concentration of a chemical component and absorbance; a server that acquires the information regarding the type and proportion of the chemical component, the information being stored in the database; an arithmetic and control unit disposed in a control center, the arithmetic and control unit calculating the concentration of the chemical component in the water system on the basis of the measured absorbance and the calibration curve or the concentration of the water treatment chemical on the basis of the concentration of the chemical component; and the communication device that sends the absorbance of light received from the sending unit of the water analyzer to the arithmetic and control unit and receives the concentration of the chemical component calculated in the arithmetic and control unit or the concentration of the water treatment chemical calculated in the arithmetic and control unit on the basis of the concentration of the chemical component. The arithmetic and control unit calculates the concentration of the chemical component in the water system on the basis of the calibration curve corresponding to the chemical component acquired from the database and the absorbance sent from the communication device.

A system for calculating a concentration of a water treatment chemical of a third invention includes a water analyzer including an absorbance measuring device for measuring absorbance of water taken from a water system containing a water treatment chemical, and a sending unit that sends the measured absorbance to a communication device; a database that stores a type and proportion of a chemical component of the water treatment chemical and a calibration curve defining a relationship between a concentration of a chemical component and absorbance; a server that sends the information regarding the type and proportion of the chemical component to the communication device, the information being stored in the database; and the communication device including an arithmetic and control unit that calculates the concentration of the chemical component in the water system on the basis of the measured absorbance and the calibration curve or the concentration of the water treatment chemical on the basis of the concentration of the chemical component. The arithmetic and control unit receives a calibration curve corresponding to the chemical component contained in information stored in the database from the server, and calculates the concentration of the chemical component in the water system on the basis of the calibration curve and the absorbance sent from the sending unit of the water analyzer.

It is preferable in the system for calculating a concentration of a water treatment chemical that the arithmetic and control unit calculates the concentration of the water treatment chemical in the water system on the basis of the concentration of the chemical component and the proportion of the chemical component, the proportion of the chemical component being acquired from the database.

According to one aspect of the invention, the component is a polymer especially an anionic polymer.

When the polymer is an anionic polymer, it is preferable that the water analyzer includes an adder for adding a detection reagent such as quaternary ammonium salt to water that is to be analyzed.

The water analyzer preferably includes a display unit that displays the concentration calculated by the arithmetic and control unit.

A fourth invention provides a method for calculating a concentration of a water treatment chemical in which a concentration of a chemical component in a water system is computed on the basis of the results of measurement of absorbance of a water system, the measurement being conducted by using a water analyzer. The water analyzer includes an arithmetic and control unit, and a storage unit that stores a calibration curve defining the relationship between the concentration of a chemical component and absorbance. The calibration curve corresponds to the chemical component of the water treatment chemical. The method includes a step in which a server acquires information regarding the type and proportion of the chemical component of the water treatment chemical, the information being stored in a database, and sends the information to a communication device; a step in which the communication device sends the information regarding the type and proportion of the chemical component to the water analyzer, the information being acquired from the server; and a step in which the arithmetic and control unit acquires a calibration curve contained in information received from the communication device, the calibration curve corresponding to the chemical component, and calculates the concentration of the chemical component in the water system on the basis of the calibration curve and the measured absorbance.

A fifth invention provides a method for calculating a concentration of a water treatment chemical in which a concentration of a chemical component in a water system is computed on the basis of the results of measurement of absorbance by the water system, the measurement being conducted by using a water analyzer. The method includes a step in which absorbance of a water system is sent to a communication device, the absorbance being measured by using a water analyzer; a step in which the communication device sends the absorbance to an arithmetic and control unit disposed in a control center; a step in which the arithmetic and control unit acquires information regarding the type and proportion of a chemical component of the water treatment chemical and a calibration curve defining a relationship between a concentration of a chemical component and absorbance from a database, the calibration curve corresponding to a chemical component of the water treatment chemical, and calculates the concentration of the chemical component in the water system on the basis of the acquired calibration curve and the received absorbance; and a step in which the calculation results are sent to the communication device.

A sixth invention provides a method for calculating a concentration of a water treatment chemical in which the concentration of a chemical component in a water system is computed on the basis of results of measurement of absorbance in the water system, the measurement being conducted by using a water analyzer. The method includes a step in which the absorbance measured by the water analyzer is sent to an arithmetic and control unit disposed in a communication device; a step in which a server acquires information regarding the type and proportion of a chemical component of the water treatment chemical and a calibration curve defining a relationship between concentration and absorbance from a database, the calibration curve corresponding to the chemical component of the water treatment chemical, and sends the information to the communication device; and a step in which the arithmetic and control unit calculates the concentration of the chemical component in the water system on the basis of the calibration curve and absorbance received.

It is preferable in the method for calculating a concentration of a water treatment chemical according to the fourth to sixth invention that the arithmetic and control unit calculates the concentration of the water treatment chemical in the water system on the basis of the concentration of the chemical component and the proportion of the chemical component, the proportion of the chemical component being received from the communication device.

The method for calculating the concentration of a water treatment chemical according to an aspect of the present invention further includes a step in which the information regarding the type and proportion of the component of the water treatment chemical is changed, the information being stored in the database.

The method for calculating a concentration of a water treatment chemical according to an aspect of the present invention, further includes a step in which the results of calculation of concentration are sent from the communication device to the water analyzer.

Advantageous Effects of Invention

In the present invention, a coloring reagent (including one used for making test water cloudy) is preferably added to test water taken from a water system, and absorbance by the test water is measured. Subsequently, the concentration of a chemical component in the water system is determined on the basis of the absorbance and a calibration curve acquired from a database. Then, the concentration of a chemical in the water system can be calculated on the basis of the concentration and proportion of the chemical component which are acquired from the database.

Thus, according to the present invention, it is possible to readily calculate the concentration of a chemical component or water treatment chemical charged in a water system.

DESCRIPTION OF EMBODIMENTS

Embodiments of the present invention are described below with reference to the attached drawings.

Figure 1:
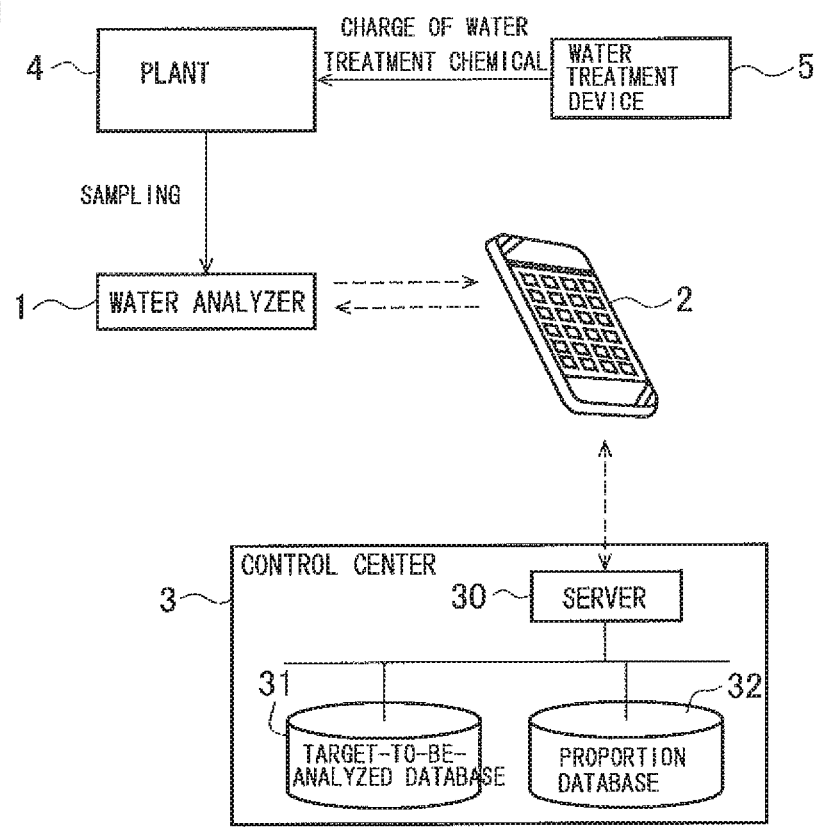
FIG. 1 is a diagram schematically illustrating a system for calculating the concentration of a water treatment chemical according to an embodiment of the present invention.

FIG. 1 schematically illustrates a system for calculating the concentration of a water treatment chemical according to an embodiment of the present invention. The system for calculating the concentration of a water treatment chemical includes a water analyzer 1 that analyzes the quality of water taken (i.e., sampled) from a plant 4, a communication device 2, and a control center 3. The plant 4 is a plant in which water is used. The water used in the plant 4 is treated by a water treatment device 5.

For example, the plant 4 may be a cooling tower, and the water treatment device 5 may be a chemical-injecting device that injects a water treatment chemical such as a scale inhibitor, a slime inhibitor, or an anticorrosive into water passing through the cooling tower in order to prevent the cooling water system from being contaminated or pipes from being corroded. Blow water discharged from the cooling tower, circulating water that circulates inside the cooling tower, and make-up water fed into the cooling tower may be sampled, and the quality of the sampled water is analyzed by the water analyzer 1. The plant 4 is not limited to a cooling tower and may be a water system plant such as a boiler water system, a dust collection water system, a water system used in pulp and paper factories, or a water system used in iron-making factories.

As illustrated in FIG. 1, the control center 3 includes a server 30, a target-to-be-analyzed database 31, and a proportion database 32. The target-to-be-analyzed database 31 registers (i.e., stores) information regarding one or a plurality of components of each of various water treatment chemicals and, among the plurality of components, components which are to be analyzed by the water analyzer 1.

The target-to-be-analyzed database 31 may store information regarding the types of water treatment chemicals charged in the plant 4. While the number of the plant 4 illustrated in FIG. 1 is one, a plurality of plants 4 may be arranged at different positions. The target-to-be-analyzed database 31 may store the types of the water treatment chemicals charged in each of the plurality of plants 4.

The proportion database 32 registers (i.e., stores) the proportions of components of each of a plurality of water treatment chemicals which are to be analyzed by the water analyzer 1. Table 1 summarizes an example of information registered in the proportion database 32.

TABLE 1

| Name of water treatment chemical | Proportion of polymer A (%) | Proportion of polymer B (%) | Proportion of polymer C (%) |
| --- | --- | --- | --- |
| A1 | 10 | — | — |
| A2 | 15 | — | — |
| B1 | — | 10 | — |
| C1 | — | — | 10 |
| D1 | 10 | 5 | — |

The proportion database 32 may store not only the proportions (i.e., contents) of the components that are to be analyzed by the water analyzer 1, but also the proportions of all the components.

The data registered in the target-to-be-analyzed database 31 and the data registered in the proportion database 32 are each updated at a predetermined timing. The data may be updated manually by an operator or automatically. The data update enables, when the types or proportions of the components of a water treatment chemical have changed, the target-to-be-analyzed database 31 and the proportion database 32 to be immediately updated with the new information.

The server 30 of the control center 3 is capable of communicating with the communication device 2. Upon receiving a request from the communication device 2, the server 30 acquires data from the target-to-be-analyzed database 31 and the proportion database 32 and sends the data to the communication device 2. For example, upon being notified of the name of a water treatment chemical and receiving a request for information regarding the water treatment chemical from the communication device 2, the server 30 retrieves information regarding the type and proportion of the component that is to be analyzed of the water treatment chemical from the target-to-be-analyzed database 31 and proportion database 32 and sends the information to the communication device 2.

Alternatively, upon being notified of information identifying the plant 4 from the communication device 2, the server 30 may retrieve information regarding the plant 4 from the target-to-be-analyzed database 31 and the proportion database 32 to specify the water treatment chemical charged in the plant 4 and send the information regarding the types and proportions of the components that are to be analyzed of the water treatment chemical to the communication device 2.

The communication device 2 illustrated in FIG. 1 acquires information regarding the types and proportions of the components that are to be analyzed by the water analyzer 1 which are contained in the water treatment chemical charged in the plant 4 from the server 30 of the control center 3 and sends (i.e., transfers) the information to the water analyzer 1.

Figure 2:
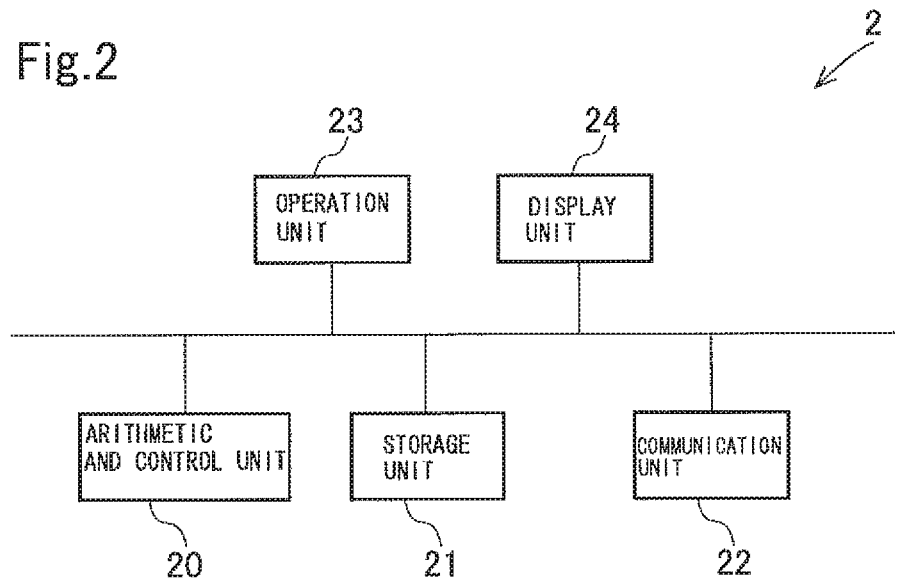
FIG. 2 is a diagram schematically illustrating a communication device used in an embodiment of the present invention.

FIG. 2 schematically illustrates the communication device 2. As illustrated in FIG. 2, the communication device 2 includes an arithmetic and control unit 20, a storage unit 21, a communication unit 22, an operation unit 23, and a display unit 24. Examples of the communication device 2 include a smart phone and a tablet personal computer. The communication unit 22 is capable of wireless or wire communication and communicates with the server 30 via the Internet. The communication unit 22 is also capable of communicating with the water analyzer 1 via a serial communication cable, that is, wire communication, or via a wireless LAN, that is, wireless communication.

The operation unit 23 receives instructions given by an operator. The display unit 24 is a liquid crystal display or the like and capable of displaying various types of information. The operation unit 23 and the display unit 24 may constitute a touch panel.

On the basis of the instructions given by an operator via the operation unit 23, the arithmetic and control unit 20 sends a request for information regarding the types and proportions of the components that are to be analyzed of the water treatment chemical charged in the plant 4 to the server 30 via the communication unit 22. Upon receiving the information regarding the types and proportions of the components that are to be analyzed from the server 30 via the communication unit 22, the arithmetic and control unit 20 stores the acquired information in the storage unit 21. Subsequently, on the basis of the instructions given by an operator via the operation unit 23, the arithmetic and control unit 20 sends the information acquired from the server 30 to the water analyzer 1 via the communication unit 22.

The water analyzer 1 illustrated in FIG. 1 determines the quality of test water sampled from the plant 4 on the basis of the information received from the communication device 2 and analyzes at least one component such as a polymer or a germicide.

Figure 3:
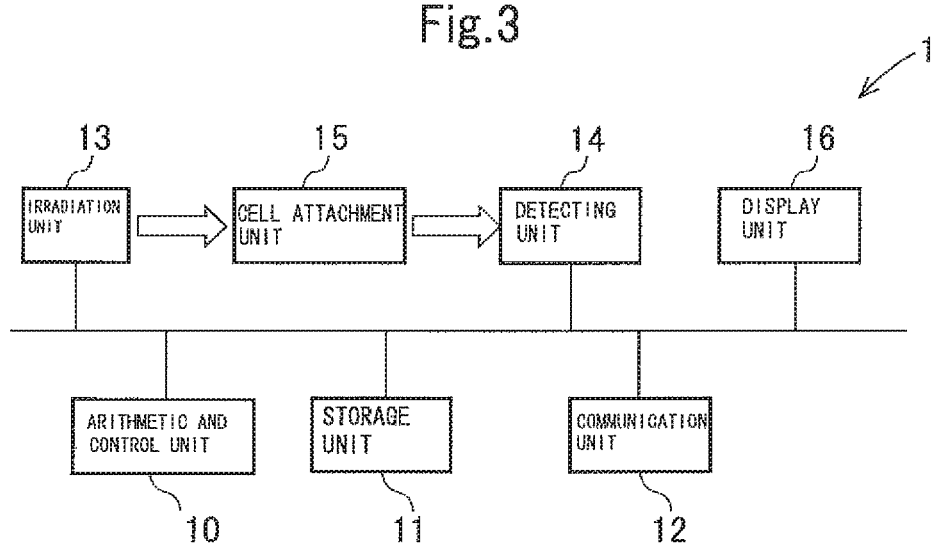
FIG. 3 is a diagram schematically illustrating a water analyzer used in an embodiment of the present invention.

FIG. 3 schematically illustrates the water analyzer 1. The water analyzer 1 includes an arithmetic and control unit 10, a storage unit 11, a communication unit 12, an irradiation unit 13, a detecting unit 14, a cell attachment unit 15, and a display unit 16. The water analyzer 1 is a portable and small analyzer. The water analyzer 1 may be, for example, a spectro photometer that determines the concentration of a chemical in test water on the basis of absorbance.

The storage unit 11 stores the calibration curves corresponding to the respective components that are to be analyzed. The calibration curves are each prepared by measuring reference solutions having known concentrations in the order of increasing concentrations and plotting absorbance against concentration. For example, the storage unit 11 stores different calibration curves corresponding to the respective types of polymers.

The storage unit 11 also stores information received from the communication device 2 via the communication unit 12 (i.e., information regarding the types and proportions of components that are to be analyzed of a water treatment chemical charged in the plant 4).

The communication unit 12 is capable of communicating with the communication device 2 by wire communication or wireless communication.

To the cell attachment unit 15, a measurement cell (not illustrated in the drawing), in which test water taken from the plant 4 is to be charged, can be attached. In this embodiment, a measurement cell equipped with a lid is attached to the cell attachment unit 15. The cell attachment unit 15 is provided with a light-shielding cap (not illustrated in the drawing).

The irradiation unit 13 produces light (i.e., monochromatic light) having a desired wavelength by dispersing light emitted from a light source through a diffraction grating and irradiates the measurement cell attached to the cell attachment unit 15 with the monochromatic light. Examples of the light source include a halogen lamp and a xenon flash lamp. An LED having a specific wavelength may also be used. The light produced is, for example, visible light having a wavelength of 400 to 900 nm.

Upon being irradiated by the irradiation unit 13, the detecting unit 14 detects the light that transmitted (or, light scattered) through the measurement cell. The detecting unit 14 may include a silicon photodiode or the like.

The arithmetic and control unit 10 calculates absorbance from the results of detection conducted by the detecting unit 14. For example, the arithmetic and control unit 10 measures the amount of current or voltage generated in the silicon photodiode of the detecting unit 14, determines the intensity of the light received by the detecting unit 14, and thereby calculates absorbance.

The arithmetic and control unit 10 calculates the concentration of the component that is to be analyzed from the calculated absorbance with reference to a calibration curve stored in the storage unit 11. The arithmetic and control unit 10 also calculates the concentration of the water treatment chemical on the basis of the proportion of the component that is to be analyzed in the water treatment chemical which is stored in the storage unit 11.

The display unit 16 is a liquid crystal display or the like and displays the results of the calculation conducted by the arithmetic and control unit 10.

The concentration of an anionic polymer in water can be measured with the water analyzer 1 by using a quaternary ammonium salt as an analytical reagent (i.e., coloring reagent) by the following method.

Examples of the quaternary ammonium salt include benzethonium salts, tetraalkylammonium salts, trialkylbenzylammonium salts, benzalkonium salts, alkylpyridinium salts, and imidazolium salts. Examples of the types of the salts include a chloride, a bromide, an iodide, and a sulfate.

The water analyzer 1 is brought into the vicinity of the water system that is to be measured. Test water is taken from the targeted water system and charged into a measurement cell. The test water is manually collected. The amount of test water may be small, that is, specifically, about a few milliliters to several tens of milliliters.

The measurement cell is attached to the cell attachment unit 15. After the entirety of the cell attachment unit 15 is covered with the light-shielding cap, the measurement cell is irradiated with visible light having a wavelength of 400 to 900 nm, and the absorbance of the visible light is measured. This operation is conducted in order to perform zero-correction of the measurement apparatus.

Subsequently, the light-shielding cap is removed, and the measurement cell is detached. The lid of the measurement cell is opened, and an aqueous solution of a quaternary ammonium salt is added to the measurement cell. The content of the quaternary ammonium salt in the test water is generally set to about 50 to 4000 mg/l.

In the present invention, although it is possible to perform sufficient turbidimetry by adding only a quaternary ammonium salt, a chelating agent may optionally be further added to the test water in order to increase the stability of cloudiness of the test water subjected to turbidimetry.

Specific examples of the chelating agent include ethylenediamine tetraacetate, nitrilotriacetate, citrates, and malates.

When the chelating agent is used in combination, the content of the chelating agent is generally set to about 1000 to 5000 mg/l. The chelating agent may be added to the test water at the same time as the reagent. In another case, after the chelating agent has been added to the test water, the quaternary ammonium salt may be added to the test water. After the above reagent and the like have been added to the test water, the measurement cell is again covered with a lid, shaken a few times in order to perform stirring, again attached to the optical measurement unit of the main body, and covered with the light-shielding cap. The test water is generally left standing for about five minutes, which is the time required for a reaction.

As a result of the above reaction, the anionic polymer contained in the test water makes the test water cloudy. After the elapse of a predetermined amount of time from the addition of the reagent, the measurement cell is attached to the cell attachment unit 15, and absorbance is measured.

The analytical reagent is not limited to the above-mentioned reagents. The zero-correction of the measurement apparatus used in the present invention may be omitted in the case where the concentration of the reagent is controlled such that absorbance by the target that is to be measured achieves a sufficient SN ratio even when the zero-correction is omitted.

Figure 4:
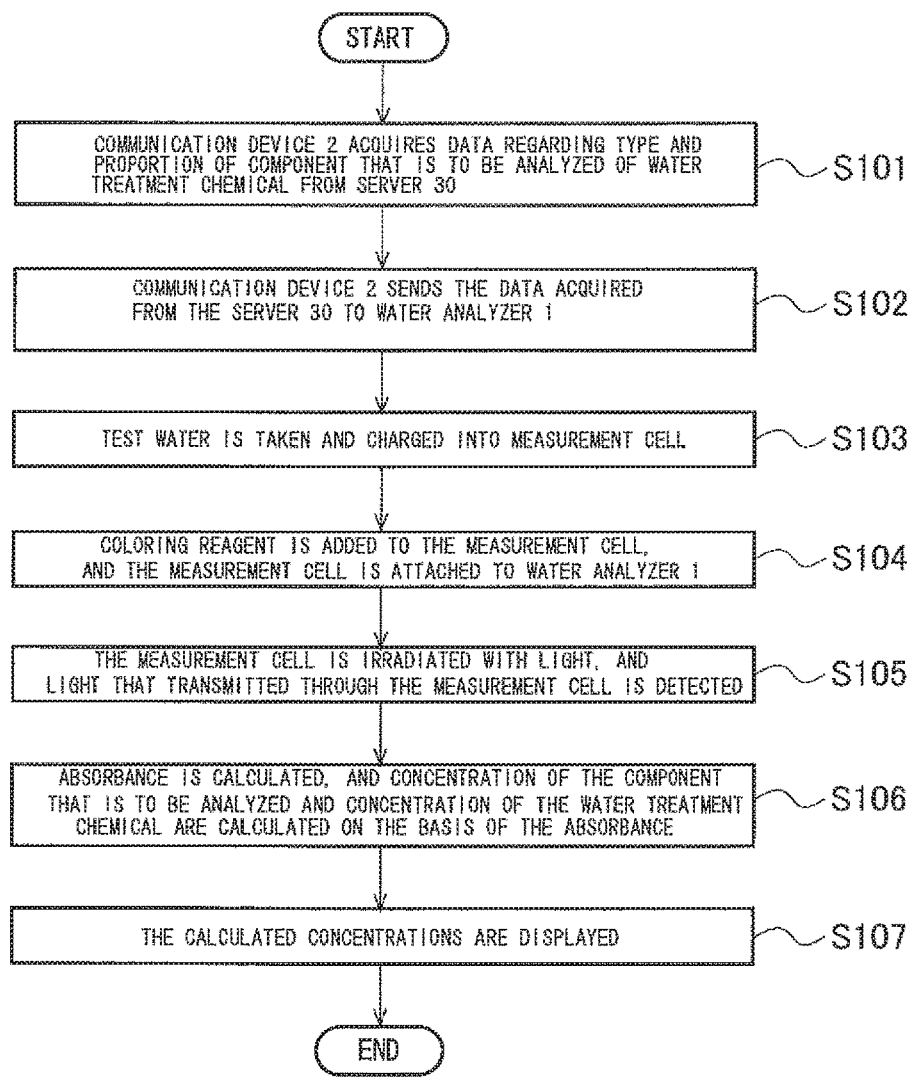
FIG. 4 is a flowchart used for explaining a method for calculating the concentration of a water treatment chemical according to an embodiment of the present invention.

On the basis of the absorbance data acquired in the above-described manner, the concentration of a water treatment chemical is calculated by the following method, which is explained using the flowchart illustrated in FIG. 4.

[Step S101] Information regarding the type and content of a component that is to be analyzed of a water treatment chemical charged in the plant 4, which is the target plant whose water quality is to be measured, is acquired from the server 30 of the control center 3 by using the communication device 2. For example, the communication device 2 acquires, from the server 30, information that the component that is to be analyzed of the water treatment chemical charged in the plant 4 is an anionic polymer and the proportion of the anionic polymer in the water treatment chemical.

[Step S102] The data acquired from the server 30 in Step S101 is transferred to the water analyzer 1 by using the communication device 2. Thus, the latest information regarding the type and proportion of the component of the water treatment chemical charged in the plant 4 is registered in the water analyzer 1. For example, the type and proportion of an anionic polymer contained in the water treatment chemical are registered in the water analyzer 1.

[Step S103] The water analyzer 1 is brought into the vicinity of the plant 4. Test water is taken from the plant 4 and charged into a measurement cell of the water analyzer 1.

[Step S104] A coloring reagent corresponding to the component that is to be analyzed of the test water is added to the measurement cell. For example, as described above, a quaternary ammonium salt such as a benzethonium salt may be used as a reagent capable of reacting with the anionic polymer.

After the addition of the coloring reagent, the measurement cell is covered with a lid, shaken a few times in order to perform stirring, and subsequently attached to the cell attachment unit 15 of the water analyzer 1.

[Step S105] Upon the irradiation unit 13 irradiating the measurement cell with light, the detecting unit 14 detects the light that transmitted through the measurement cell.

[Step S106] The arithmetic and control unit 10 calculates absorbance on the basis of the results of the detection conducted by the detecting unit 14 in Step S105. The arithmetic and control unit 10 identifies the component that is to be analyzed of the water treatment chemical on the basis of the data transferred from the communication device 2 in Step S102 and acquires a calibration curve corresponding to the component from the storage unit 11. The arithmetic and control unit 10 calculates the concentration of the component that is to be analyzed of the test water on the basis of the calculated absorbance with reference to the calibration curve acquired from the storage unit 11. For example, the arithmetic and control unit 10 calculates the concentration of an anionic polymer in the test water.

The arithmetic and control unit 10 also acquires the proportion of the component that is to be analyzed in the water treatment chemical from the data transferred from the communication device 2 in Step S102 and calculates the concentration of the water treatment chemical in the test water on the basis of the concentration and proportion of the component that is to be analyzed.

[Step S107] The display unit 16 displays the concentration calculated by the arithmetic and control unit 10 in Step S106.

As described above, in this embodiment, the communication device 2 acquires information regarding the type and proportion of a component of a water treatment chemical charged in the plant 4 from the server 30 of the control center 3 and registers the information in the water analyzer 1. The water analyzer 1 calculates the concentration of the component that is to be analyzed by using a calibration curve registered by the communication device 2 which corresponds to the component of the water treatment chemical. This may reduce the chance of an error in selecting a calibration curve and enable the concentration of the component to be calculated with accuracy. Furthermore, the water analyzer 1 is capable of readily calculating the concentration of the water treatment chemical with accuracy by using the proportion of the component that is to be analyzed in the water treatment chemical which is registered by the communication device 2.

In the case where the type or proportion of the component of the water treatment chemical has changed, the database of the control center 3 is immediately updated with the change. The communication device 2 acquires the latest information regarding the type and proportion of the component of the water treatment chemical and registers the latest information in the water analyzer 1. This enables the water analyzer 1 to calculate the concentration of the component that is to be analyzed by automatically selecting a proper calibration curve. This also enables the water analyzer 1 to calculate, with accuracy, the concentration of the water treatment chemical on the basis of the changed proportion of the component that is to be analyzed.

As described above, according to the embodiment, it is possible to readily measure or calculate the concentrations of various water treatment chemicals in a water system with accuracy. It is also possible to readily control the concentrations of water treatment chemicals in a plant. In this embodiment, information regarding the types and proportions of the components of a water treatment chemical is stored in the database of the control center 3 instead of on paper. This may strengthen information security.

In the above-described embodiment, an example case is described where calibration curves corresponding to the respective components that are to be analyzed are stored in the storage unit 11 of the water analyzer 1. It is also possible to send a calibration curve corresponding to a new component that is to be analyzed from the server 30 of the control center 3 to the communication device 2, transfer the new calibration curve from the communication device 2 to the water analyzer 1, and register the new calibration curve in the storage unit 11.

In the above-described embodiment, the arithmetic and control unit disposed in the water analyzer 1 calculates, by using a calibration curve, the concentration of the component that is to be analyzed. Alternatively, the calibration curve corresponding to the component of the water treatment chemical may be stored in the database of the control center instead of the portable water analyzer and the arithmetic and control unit may be disposed in the control center 3 or the communication device 2. In such a case, the type of the chemical component, the absorbance, and the like, which are measured by the portable water analyzer, are sent to the communication device 2 or the control center 3. Furthermore, the concentration of the chemical component or the chemical which is calculated in the control center 3 or the communication device 2 is sent to the water analyzer 1 or the communication device (e.g., smart phone) 2 and displayed on a display thereof.

In the case where the calculation of concentration is conducted in the control center 3, the water analyzer 1 sends the measured absorbance to the communication device 2, and the communication device 2 sends the absorbance received from the water analyzer 1 to the server 30 of the control center 3. The control center 3 includes a database that stores data regarding calibration curves corresponding to the respective components that are to be analyzed and the proportions of the components, an arithmetic and control unit that conducts calculation of concentration, and the like.

In the case where the arithmetic and control unit is disposed in the communication device 2 and the calculation of concentration is conducted in the communication device 2, the control center 3 includes a database that stores data regarding calibration curves corresponding to the respective components that are to be analyzed and the proportions of the components. The water analyzer 1 sends the measured absorbance to the communication device 2. The communication device 2 receives, via the server, the data regarding the calibration curves and the proportions of the components which are acquired from the database of the control center.

Even in the case where the arithmetic and control unit is disposed in the control center 3 or the communication device 2, the arithmetic and control unit calculates the concentration of the component that is to be analyzed, on the basis of absorbance and a calibration curve corresponding to the component that is to be analyzed of the water treatment chemical charged in the plant 4 as in the above-described embodiment. The arithmetic and control unit also calculates the concentration of the water treatment chemical by using the data registered in the proportion database 32. The calculation results may be displayed on the display unit 24 of the communication device 2 (in the case where the arithmetic and control unit is disposed in the control center, the server 30 notifies the communication device 2 of the calculation results). Alternatively, the calculation results may be transferred from the communication device 2 to the water analyzer 1 and displayed on the display unit 16 of the water analyzer 1.

In any of the above-described embodiments, the water analyzer 1 may have a waterproof structure in order to endure immersion measurement. Two or more components may be analyzed with the water analyzer 1.

In the above-described embodiments, information regarding the coloring reagent that is to be added to the measurement cell may be registered in the target-to-be-analyzed database 31 of the control center 3 and sent from the server 30 to the communication device 2 together with the information regarding the type and proportion of the component that is to be analyzed. This enables an operator to readily determine the type of coloring reagent that is to be used by checking the information regarding the coloring reagent which is displayed on the display unit 24 of the communication device 2.

Optionally, a barcode containing information that identifies the coloring reagent or an IC tag storing such information may be attached to the container of the coloring reagent such that a component that is to be analyzed corresponding to the coloring reagent is readily determined by reading the information with a reading unit included in the water analyzer 1 or the communication device 2.

At least a part of the system for calculating the concentration of a water treatment chemical which is described in the above-described embodiments may be constituted by hardware or software. In the case where software is used, a program that realizes at least a part of the function of the system for calculating the concentration of a water treatment chemical may be stored in a recording medium such as a flexible disk or a CD-ROM and executed by being loaded into a computer. Examples of the recording medium are not limited to only detachable recording media such as a magnetic disk and an optical disk, but also include fixed recording media such as a hard disk drive or a memory.

The program that realizes at least a part of the function of the system for calculating the concentration of a water treatment chemical may be distributed via telecommunication lines (including wireless communication) such as the Internet. The program may be distributed via a wire circuit or wireless circuit, such as the Internet, or by being stored in a recording medium after being encrypted, modulated, or compressed.

The foregoing embodiments are merely examples of the present invention. The system for calculating the concentration of a water treatment chemical according to the present invention may have a structure other than those described in the foregoing embodiments.

Although the present invention has been described in detail with reference to particular embodiments, it is apparent to a person skilled in the art that various modifications can be made therein without departing from the spirit and scope of the present invention.

The present application is based on Japanese Patent Application No. 2013-255090 filed on Dec. 10, 2013, which is incorporated herein by reference in its entirety.

REFERENCE SIGNS LIST

1 WATER ANALYZER
2 COMMUNICATION DEVICE
3 CONTROL CENTER
4 PLANT
5 WATER TREATMENT DEVICE
10 ARITHMETIC AND CONTROL UNIT
11 STORAGE UNIT
12 COMMUNICATION UNIT
13 IRRADIATION UNIT
14 DETECTING UNIT
15 CELL ATTACHMENT UNIT
16 DISPLAY UNIT
20 ARITHMETIC AND CONTROL UNIT
21 STORAGE UNIT
22 COMMUNICATION UNIT
23 OPERATION UNIT
24 DISPLAY UNIT
30 SERVER
31 TARGET-TO-BE-ANALYZED DATABASE
32 PROPORTION DATABASE

The invention claimed is:

1. A system for calculating a concentration of a water treatment chemical, the system comprising:
a water analyzer including an absorbance measuring device configured for measuring absorbance of water taken from a water system containing a water treatment chemical;
a database configured to store information regarding a type and proportion of a chemical component of the water treatment chemical;
a server configured to send the information regarding the type and proportion of the chemical component of the water treatment chemical to a communication device, the information being stored in the database; and
the communication device configured to acquire the information regarding the type and proportion of the chemical component from the server and send the acquired information to the water analyzer,
the water analyzer further including:
a storage unit configured to store a calibration curve defining a relationship between a concentration of a chemical component and absorbance,
a communication unit configured to receive the information regarding a type and proportion of a chemical component of the water treatment chemical from the communication device, and
an arithmetic and control unit configured to acquire a calibration curve from the storage unit, the calibration curve corresponding to the type of the chemical component contained in the received information, and configured to calculate a concentration of the chemical component in the water system with reference to the acquired calibration curve and the measured absorbance or a concentration of the water treatment chemical on the basis of the concentration of the chemical component.

2. The system for calculating the concentration of a water treatment chemical according to claim 1, wherein the arithmetic and control unit is configured to calculate the concentration of the water treatment chemical in the water system on the basis of the concentration of the chemical component and the proportion of the chemical component, the proportion of the chemical component being received by the communication unit.

3. The system for calculating the concentration of a water treatment chemical according to claim 1, wherein the server is configured to send data regarding a calibration curve corresponding to the chemical component of the water treatment chemical to the communication device, wherein the communication device is configured to send the data regarding the calibration curve to the water analyzer, the data being received from the server, and
wherein the water analyzer is configured to register the data regarding the calibration curve in the storage unit, the data being received from the communication device via the communication unit.

4. A system for calculating a concentration of a water treatment chemical, the system comprising:
a water analyzer including absorbance measuring means configured for measuring absorbance of water taken from a water system containing a water treatment chemical, and a sending unit configured to send the measured absorbance to a communication device;
a database configured to store information regarding a type and proportion of a chemical component of the water treatment chemical and a calibration curve defining a relationship between a concentration of a chemical component and absorbance;
a server configured to acquire the information regarding the type and proportion of the chemical component, the information being stored in the database;
an arithmetic and control unit disposed in a control center, the arithmetic and control unit configured to calculate a concentration of the chemical component in the water system on the basis of the measured absorbance and the calibration curve or a concentration of the water treatment chemical on the basis of the concentration of the chemical component; and the communication device is configured to send the absorbance received from the sending unit of the water analyzer to the arithmetic and control unit and is configured to receive the concentration of the chemical component calculated in the arithmetic and control unit or the concentration of the water treatment chemical calculated in the arithmetic and control unit on the basis of the concentration of the chemical component, wherein the arithmetic and control unit is configured to calculate the concentration of the chemical component in the water system on the basis of the calibration curve corresponding to the chemical component acquired from the database and the absorbance sent from the communication device or the concentration of the water treatment chemical on the basis of the concentration of the chemical component.

5. A system for calculating a concentration of a water treatment chemical, the system comprising:

a water analyzer including an absorbance measuring device configured for measuring absorbance of water taken from a water system containing a water treatment chemical, and a sending unit that sends the measured absorbance to a communication device;

a database configured to store a type and proportion of a chemical component of the water treatment chemical and a calibration curve defining a relationship between a concentration of a chemical component and absorbance;

a server configured to send the information regarding the type and proportion of the chemical component to the communication device, the information being stored in the database; and the communication device including an arithmetic and control unit configured to calculate the concentration of the chemical component in the water system on the basis of the measured absorbance and the calibration curve or the concentration of the water treatment chemical on the basis of the concentration of the chemical component, wherein the arithmetic and control unit is configured to receive a calibration curve corresponding to the chemical component contained in information stored in the database from the server, and is configured to calculate the concentration of the chemical component in the water system on the basis of the calibration curve and the absorbance sent from the sending unit of the water analyzer or the concentration of the water treatment chemical on the basis of the concentration of the chemical component.

6. The system for calculating the concentration of a water treatment chemical according to claim 4, wherein the arithmetic and control unit is configured to calculate the concentration of the water treatment chemical in the water system on the basis of the concentration of the chemical component and the proportion of the chemical component, the proportion of the chemical component being acquired from the database.

7. The system for calculating the concentration of a water treatment chemical according to a claim 4, wherein the communication device is configured to send the concentration of the chemical component or the concentration of the water treatment chemical to the water analyzer, the concentration of the water treatment chemical being calculated from the concentration of the chemical component.

8. The system for calculating the concentration of a water treatment chemical according to claim 1. wherein the component is a polymer.

9. The system for calculating the concentration of a water treatment chemical according to claim 8, wherein the polymer is an anionic polymer, and the water analyzer includes a reagent adder configured for adding a detection reagent including one used for making the water cloudy and configured for coloring the water.

10. The system for calculating the concentration of a water treatment chemical according to claim 1, wherein the water analyzer includes a display unit configured to display the concentration calculated by the arithmetic and control unit.

11. A method for calculating a concentration of a water treatment chemical in which a concentration of a chemical component in a water system is computed on the basis of results of measurement of absorbance by a water system, the measurement being conducted by using a water analyzer, the water analyzer including an arithmetic and control unit, and a storage unit that stores a calibration curve defining a relationship between a concentration of a chemical component and absorbance, the calibration curve corresponding to the chemical component of the water treatment chemical, the method comprising:

a step in which a server acquires information regarding the type and proportion of the chemical component of the water treatment chemical, the information being stored in a database, and sends the information to a communication device;

step in which the communication device sends the information regarding the type and proportion of the chemical component to the water analyzer, the information being acquired from the server; and a step in which the arithmetic and control unit acquires a calibration curve contained in information received from the communication device, the calibration curve corresponding to the chemical component, and calculates the concentration of the chemical component in the water system on the basis of the calibration curve and the measured absorbance.

12. A method for calculating a concentration of a water treatment chemical in which a concentration of a chemical component in a water system is computed on the basis of results of measurement of absorbance by the water system, the measurement being conducted by using a water analyzer, the method comprising:

a step in which absorbance by a water system is sent to a communication device, the absorbance being measured by using the water analyzer;

a step in which the communication device sends the absorbance to an arithmetic and control unit disposed in a control center;

a step in which the arithmetic and control unit acquires information regarding the type and proportion of a chemical component of the water treatment chemical and a calibration curve defining a relationship between a concentration of a chemical component and absorbance from a database, the calibration curve corresponding to a chemical component of the water treatment chemical, and calculates a concentration of the chemical component in the water system on the basis of the acquired calibration curve and the received absorbance; and a step in which the calculation results are sent to the communication device.

13. A method for calculating a concentration of a water treatment chemical in which a concentration of a chemical component in a water system is computed on the basis of results of measurement of absorbance of the water system, the measurement being conducted by using a water analyzer, the method comprising:
- a step in which the absorbance measured by the water analyzer is sent to an arithmetic and control unit disposed in a communication device;
- a step in which a server acquires information regarding the type and proportion of a chemical component of the water treatment chemical and a calibration curve defining the relationship between concentration and absorbance from a database, the calibration curve corresponding to the chemical component of the water treatment chemical, and sends the information to the communication device; and
- a step in which the arithmetic and control unit calculates the concentration of the chemical component in the water system on the basis of the calibration curve and absorbance received.

14. The method for calculating a concentration of a water treatment chemical according to claim 11, wherein the arithmetic and control unit calculates the concentration of the water treatment chemical in the water system on the basis of the concentration of the chemical component and the proportion of the chemical component, the proportion of the chemical component being received from the communication device.

15. The method for calculating a concentration of a water treatment chemical according to claim 11, the method further comprising a step in which the information regarding the type and proportion of the component of the water treatment chemical is changed, the information being stored in the database.

16. The method for calculating a concentration of a water treatment chemical according to claim 11, the method further comprising a step in which the results of calculation of concentration are sent from the communication device to the water analyzer.

17. The method for calculating a concentration of a water treatment chemical according to claim 12, wherein the arithmetic and control unit calculates the concentration of the water treatment chemical in the water system on the basis of the concentration of the chemical component and the proportion of the chemical component, the proportion of the chemical component being received from the communication device.

18. The method for calculating a concentration of a water treatment chemical according to claim 12, the method further comprising a step in which the information regarding the type and proportion of the component of the water treatment chemical is changed, the information being stored in the database.

19. The method for calculating a concentration of a water treatment chemical according to claim 13, wherein the arithmetic and control unit calculates the concentration of the water treatment chemical in the water system on the basis of the concentration of the chemical component and the proportion of the chemical component, the proportion of the chemical component being received from the communication device.

20. The method for calculating a concentration of a water treatment chemical according to claim 13, the method further comprising a step in which the information regarding the type and proportion of the component of the water treatment chemical is changed, the information being stored in the database.

* * * * *